(12) United States Patent
Snow et al.

(10) Patent No.: US 11,510,603 B2
(45) Date of Patent: *Nov. 29, 2022

(54) DEVICE AND MEANS OF ASSESSING NEUROMUSCULAR JUNCTION STATUS WITH HIGHER FIDELITY

(71) Applicant: SafeOp Surgical, Inc., Hunt Valley, MD (US)

(72) Inventors: Robert Snow, Phoenix, MD (US); Richard O'Brien, Hunt Valley, MD (US)

(73) Assignee: SafeOp Surgical, Inc., Hunt Valley, MD (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/127,445

(22) Filed: Dec. 18, 2020

(65) Prior Publication Data

US 2021/0100490 A1 Apr. 8, 2021

Related U.S. Application Data

(63) Continuation of application No. 15/529,928, filed as application No. PCT/US2015/062754 on Nov. 25, 2015, now Pat. No. 10,869,609.

(Continued)

(51) Int. Cl.
*A61B 5/24* (2021.01)
*A61B 5/00* (2006.01)
*A61B 5/389* (2021.01)

(52) U.S. Cl.
CPC ............... *A61B 5/24* (2021.01); *A61B 5/389* (2021.01); *A61B 5/4821* (2013.01); *A61B 5/4839* (2013.01); *A61B 2505/05* (2013.01)

(58) Field of Classification Search
CPC ......... A61B 5/24; A61B 5/389; A61B 5/4821; A61B 5/4839; A61B 2505/05
See application file for complete search history.

(56) References Cited

U.S. PATENT DOCUMENTS 2,690,178 A 9/1954 George
3,364,929 A 1/1968 Ide et al.
(Continued)

FOREIGN PATENT DOCUMENTS

EP 1618840 A1 1/2006
EP 1656883 A1 5/2006
(Continued)

OTHER PUBLICATIONS

Ali et al. (Aug. 1976) "Monitoring of Neuromuscular Function", Anesthesiology, 45(2):216-249.
(Continued)

*Primary Examiner* — Catherine M Voorhees
(74) *Attorney, Agent, or Firm* — Mintz, Levin, Cohn, Ferris, Glovsky and Popeo, P.C.

(57) ABSTRACT

Devices and methods for stimulation and recording of muscle responses for determining degree of neuromuscular blockade, particularly relevant to elicitation of such responses in those under the influence of anesthesia. A system for estimating the degree of neuromuscular blockade includes at least one stimulating electrode, at least one recording electrode, a pulse generator for providing stimulation to a nerve through the stimulating electrode, and a computing device configured to: apply stimuli to the nerve according to a stimulation protocol, wherein the stimulation protocol provides a plurality of stimulation sequences that vary in frequency of pulses in the stimulation sequence, frequency of the stimulation sequences, number of pulses in the stimulation sequence, or all of the above; measure, by the recording electrode, electrical responses of a muscle; and (Continued)

estimate the degree of neuromuscular blockade based on changes in the electrical responses of the muscle during a stimulation sequence.

26 Claims, 4 Drawing Sheets

Related U.S. Application Data

(60) Provisional application No. 62/085,193, filed on Nov. 26, 2014.

(56) References Cited

U.S. PATENT DOCUMENTS

| | | | |
|---|---|---|---|
| 3,513,834 A | 5/1970 | Suzuki et al. | |
| 3,565,080 A | 2/1971 | Ide et al. | |
| 3,774,593 A | 11/1973 | Hakata et al. | |
| 3,898,983 A | 8/1975 | Elam | |
| 3,905,355 A | 9/1975 | Brudny | |
| 3,916,876 A | 11/1975 | Freeman | |
| 4,148,303 A | 4/1979 | Cohen | |
| 4,291,705 A | 9/1981 | Severinghaus et al. | |
| 5,131,401 A | 7/1992 | Westenskow et al. | |
| 7,447,541 B2 | 11/2008 | Huiku et al. | |
| 8,401,632 B1 | 3/2013 | Stone et al. | |
| 8,412,335 B2 | 4/2013 | Gliner et al. | |
| 8,506,502 B2 | 8/2013 | Gilhuly | |
| 8,731,654 B2 | 5/2014 | Johnson et al. | |
| 10,869,609 B2 * | 12/2020 | Snow | A61B 5/389 |
| 2001/0031916 A1 | 10/2001 | Bennett et al. | |
| 2003/0088185 A1 | 5/2003 | Prass | |
| 2008/0009771 A1 | 1/2008 | Perry et al. | |
| 2009/0018610 A1 * | 1/2009 | Gharib | A61B 17/02 607/48 |
| 2010/0081963 A1 | 4/2010 | Gilhuly | |
| 2013/0053926 A1 | 2/2013 | Hincapie et al. | |
| 2013/0204155 A1 * | 8/2013 | Brull | A61B 5/4848 600/546 |
| 2014/0107524 A1 | 4/2014 | Brull et al. | |
| 2014/0188013 A1 | 7/2014 | Wijting et al. | |
| 2014/0235991 A1 | 8/2014 | Gadsby | |

FOREIGN PATENT DOCUMENTS

| | | |
|---|---|---|
| EP | 1174081 B1 | 1/2008 |
| JP | H06500932 A | 1/1994 |
| JP | 2002159497 A | 6/2002 |
| JP | 2008519609 A | 6/2008 |
| JP | 2012505707 A | 3/2012 |
| KR | 1020120096846 A | 8/2012 |
| WO | 9203974 A1 | 3/1992 |
| WO | 2005051201 A1 | 6/2005 |
| WO | 2006050586 A1 | 5/2006 |
| WO | 2014059259 A1 | 4/2014 |

OTHER PUBLICATIONS

Lien et al. (Dec. 2014) "Current Recommendations for Monitoring Depth of Neuromuscular Blockade", Current Opinion in Anesthesiology, 27(6):616-622.

* cited by examiner

DEVICE AND MEANS OF ASSESSING NEUROMUSCULAR JUNCTION STATUS WITH HIGHER FIDELITY

CROSS-REFERENCE TO RELATED APPLICATIONS

This application is a continuation of U.S. application Ser. No. 15/529,928, filed on Nov. 25, 2017, which claims priority to International Application No. PCT/US2015/062754, filed on Nov. 25, 2015, which claims the benefit of U.S. Provisional Application No. 62/085,193 filed on Nov. 26, 2014, which is hereby incorporated by reference in its entirety.

FIELD OF INVENTION

Embodiments of the present technology generally relate to the field of clinical neurophysiology. More specifically, to devices and methods for the assessment of the neuromuscular junction and the level of pharmacological blockade while under anesthesia. Such devices may be used to determine the degree of muscle relaxation both during and at the end of surgery to insure adequate surgical intervention and adequate recovery from anesthesia.

BACKGROUND OF THE INVENTION

Quantitative measurement of the depth of neuromuscular blockade during surgery and at other times is widely recognized as important, particularly to prevent residual paralysis in patients after surgery. Current techniques require the anesthesiologist to use devices that employ either mechanomyography, accelomyography, phonomyography and/or electromyography recording modalities.

All measurements of neuromuscular blockade employed by these devices depend upon stimulation of a nerve containing motor fibers and recording activity from a corresponding innervated muscle to quantify a response. Usually either the integrated compound action potential or the tension produced by a muscle in response to stimulating the ulnar nerve is recorded. A variation of the latter, developed by Viby-Mogensen, is to record the acceleration of the rate of tension development instead of the tension itself, as the two are directly proportional.

One of two strategies is typically used to determine the relative degree of muscle blockade or relaxation over time: maximal contraction determination through single or multiple stimuli to obtain a maximal muscle response that can be followed over time and fatigability or fade determination of the muscle response on repeated stimulation or after high frequency facilatory stimulation that induces tetany (post tetanic techniques). While all neuromuscular blocking compounds must produce relaxation, not all produce fade. Most, if not all, commercially available agents produce fade.

Common techniques for determining neuromuscular blockade use a standardized frequency of stimulation, both for inducing tetany and for recording muscle responses. One popular method of measuring the degree of neuromuscular blockade is the train of four (TOF) approach, characterized by four stimuli delivered at 2 Hz and measurement of both the presence or absence of responses to the stimuli, and the ratio of muscle response in amplitude—or area under the curve—of the fourth response compared to the first. The other techniques involving application of tetanic stimuli are less well understood by most anesthesiologists and therefore, infrequently or inadequately applied.

SUMMARY OF THE INVENTION

Generally, embodiments disclosed herein provide an automated device and system that follows a predetermined stimulation protocol for intermittent or continuous monitoring of the level of neuromuscular blockade throughout the surgery by automatically adjusting either the stimulation frequencies or the number of stimuli delivered according to the degree of blockade present to improve reproducibility and fidelity of the measurement. The device also uses a novel technique to more accurately reflect expected physiological strength.

The applicants have identified a need to improve measurement of strength and fatigability of the muscles and neuromuscular junctions of patients receiving neuromuscular blockade agents, and to display the data in a clear and easy to understand way. Embodiments described herein are based, at least in part, upon the applicants' discovery of the need for a simple, easy to apply device and method which automatically adjusts to the level of neuromuscular blockade, and improves reproducibility and apparentness of measurements of strength and fatigability. Such embodiments disclosed herein are particularly useful in the borderline range where current techniques, such as TOF, are less accurate and are prone to error.

Quantitative measurements typically used to measure the degree of blockade have been found to be superior to qualitative assessment of the degree of blockade by the anesthesiologist. However, the quantitative measurements achieved by existing devices and techniques may either be insufficient for determining adequate reversal of neuromuscular blockade, or not apparent enough to be clinically useful to the user. Therefore, embodiments of the present technology provide systems and methods for quantitative measurement of adequate reversal of neuromuscular junction blockade to ensure an adequate ability for the patient to breathe, and to ensure patient safety, with increased resolution and reproducibility While current recommendations suggest only a 10% degree of decrement in fourth to first response is safe in train of four (TOF) measurements (Lien 2014), even in normal muscles, responses can vary as much as 5-8% (see, e.g., Kimura 2013) to low frequency stimulation. In addition, movement artifact in the measured responses, interference from electro cautery, lower quality amplifiers and lack of adequate filtering may cause further variability. Warming of the patient after removal of the endotracheal tube may make the neuromuscular junction less efficient and shift the patient from a safe to a potentially unsafe state. These factors all make determination of safety margin difficult.

Embodiments described herein generally relate to devices and methods for measuring the degree of neuromuscular blockade in patients, particularly in the range of blockade that is borderline for safety. Various embodiments relate to devices, systems, and methods for obtaining and processing the recorded signals in such a manner that interference from electric surgical devices is reduced or eliminated while the target biosignal is maintained.

In one aspect, disclosed herein is a device for estimating the degree of neuromuscular blockade more accurately that automatically applies stimuli and measures muscle responses in varying frequency and number. In another aspect, disclosed herein is method for estimating the degree of neuromuscular blockade more accurately that automatically applies stimuli and measures muscle responses in varying frequency and number.

In another aspect, disclosed herein is a device comprising at least one stimulating electrode, at least one recording electrode, a pulse generator for providing stimulation to a nerve through the stimulating electrode, and a computing device comprising a processor having instructions stored thereon. When executed by the computing device the instructions cause the computing device to apply stimuli to the nerve through the stimulating electrode according to a stimulation protocol in varying frequency and number, measure electrical responses of a muscle, and estimate the degree of neuromuscular blockade based on changes in the electrical responses of the muscle.

In another aspect, disclosed herein is a method for estimating the degree of neuromuscular blockade, comprising applying stimuli to a nerve through a stimulating electrode according to a stimulation protocol in varying frequency and number, measuring electrical responses of a muscle, and estimating the degree of neuromuscular blockade based on changes in the electrical responses of the muscle. In some aspects, the estimation is more accurate than a standard train of four analysis. In some aspects, the method further comprises adjusting the stimulation protocol automatically according to the degree of blockade present to improve reproducibility and fidelity of the measurement.

In another aspect, disclosed herein is system comprising at least one stimulating electrode, at least one recording electrode, a pulse generator for providing stimulation to a nerve through the stimulating electrode, and a computing device comprising a processor having instructions stored thereon. When executed by the computing device, the instructions cause the computing device to apply stimuli to the nerve through the stimulating electrode according to a stimulation protocol, wherein the stimulation protocol provides a plurality of stimulation sequences that vary in frequency of pulses in the stimulation sequence, frequency of the stimulation sequences, number of pulses in the stimulation sequence, or all of the above; measure, by the recording electrode, electrical responses of a muscle; and estimate the degree of neuromuscular blockade based on changes in the electrical responses of the muscle during a stimulation sequence.

In some embodiments, estimating the degree of neuromuscular blockade comprises determining a ratio between the electrical response of the muscle from a first pulse in a stimulation sequence and the electrical response of the muscle from a last pulse in the stimulation sequence. In some embodiments, the number of pulses in a stimulation sequence is between four and twenty pulses. In some embodiments, the number of pulses increases with each subsequent stimulation sequence in the stimulation protocol. In some embodiments, the frequency of pulses in a stimulation sequences is between 2 Hz and 10 Hz. In some embodiments, the frequency of pulses increases with each subsequent stimulation sequence in the stimulation protocol.

In some embodiments, the stimulation protocol comprises a first stimulation sequence of four pulses at a first frequency, a second stimulation sequence of four pulses at a second frequency higher than the first frequency, a third stimulation sequence of four pulses at a third frequency higher than the second frequency. In some embodiments, the stimulation protocol further comprises a fourth stimulation sequence of more than four pulses.

In some embodiments, the processor further comprises instructions that when executed by the computing device, cause the computing device to function automatically, without user input. In some embodiments, the computing device automatically determines if the stimulation protocol needs to be adjusted and adjusts the stimulation protocol. In some embodiments, the computing device determines if the stimulation protocol needs to be adjusted at predetermined intervals, upon electrical response readings above or below a threshold value, in response to other physical parameters of the patient, and/or in concert with a timing of a procedure.

In some embodiments, the nerve is a peripheral nerve. In some embodiments, the peripheral nerve is at least one of the nerves in a group comprising: an ulnar nerve, a median nerve, a peroneal nerve, and a posterior tibial nerve. In some embodiments, the stimulating electrode is configured to be positioned on a wrist or an ankle of a patient.

In some embodiments, the system further comprises a display unit for displaying information about a patient. In some embodiments, the information is information related to the degree of neuromuscular blockade. In some embodiments, the system further comprises a signal amplifier to reduce factors that confound the electrical response signal, wherein the signal amplifier comprises one or more of CMRR of >96 dB, stimulation artifact filtering, and detection of electro-cautery signal.

In another aspect, disclosed herein is a method for estimating the degree of neuromuscular blockade, comprising: applying stimuli, using a pulse generator, to a nerve through a stimulating electrode according to a stimulation protocol, wherein the stimulation protocol provides a plurality of stimulation sequences that vary in frequency of pulses in the stimulation sequence, frequency of the stimulation sequences, number of pulses in the stimulation sequence, or all of the above; measuring electrical responses of a muscle; and estimating the degree of neuromuscular blockade based on changes in the electrical responses of the muscle during a stimulation sequence.

In some embodiments, estimating the degree of neuromuscular blockade comprises determining a ratio between the electrical response of the muscle from a first pulse in a stimulation sequence and the electrical response of the muscle from a last pulse in the stimulation sequence.

In some embodiments, the nerve is a peripheral nerve. In some embodiments, the peripheral nerve is at least one of the nerves in a group comprising: an ulnar nerve, a median nerve, a peroneal nerve, and a posterior tibial nerve. In some embodiments, the stimulating electrode is positioned on a wrist or an ankle of a patient.

In some embodiments, the stimulation protocol comprises a first stimulation sequence of four pulses at a first frequency, a second stimulation sequence of four pulses at a second frequency higher than the first frequency, a third stimulation sequence of four pulses at a third frequency higher than the second frequency. In some embodiments, the stimulation protocol further comprises a fourth stimulation sequence of more than four pulses.

In some embodiments, information related to the degree of neuromuscular blockade is displayed on a display unit. In some embodiments, the method further comprises determining if the stimulation protocol needs to be adjusted, based on the estimation of the degree of neuromuscular blockade, and adjusting the stimulation protocol. In some embodiments, the computing device determines if the stimulation protocol needs to be adjusted at predetermined intervals, upon electrical response readings above or below a threshold value, in response to other physical parameters of the patient, and/or in concert with a timing of a procedure.

In some embodiments, the method further comprises providing a signal amplifier to reduce factors that confound the electrical response signal, wherein the signal amplifier comprises one or more of CMRR of >96 dB, stimulation artifact filtering, and detection of electro-cautery signal.

In another aspect, disclosed herein is a device for estimating the degree of neuromuscular blockade, the device configured to provide a first set of electrical stimuli to a nerve, measure muscle responses to the stimuli, and automatically adjust the stimuli by varying the frequency of the pulses in a second set of stimuli, a number of pulses in the second set of stimuli, or both.

In another aspect, disclosed herein is a A computerized method for estimating the degree of neuromuscular blockade comprising providing a first set of electrical stimuli to a nerve, measuring muscle responses to the stimuli, and automatically adjusting the stimuli by varying the frequency of the pulses in a second set of stimuli, a number of pulses in the second set of stimuli, or both.

BRIEF DESCRIPTION OF DRAWINGS

The above-mentioned features, as well as other features, aspects, and advantages of the present technology will now be described in connection with various embodiments of the invention, in reference to the accompanying drawings. The illustrated embodiments, however, are merely examples and are not intended to limit the invention.

DETAILED DESCRIPTION OF THE INVENTION

Figure 1:
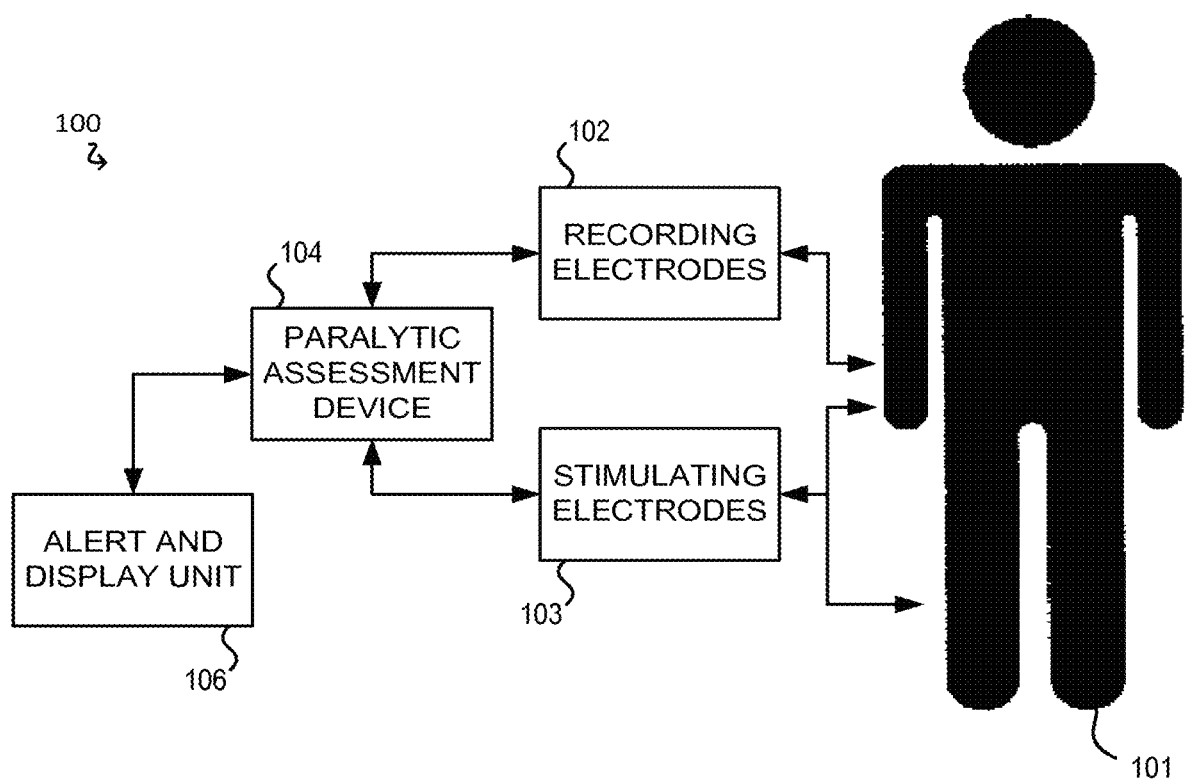
FIG. 1 depicts a functional block diagram of one embodiment of a system for monitoring and measuring the strength and fatigability of muscles and neuromuscular junctions.

In the following detailed description, reference is made to the accompanying drawings, which form part of the present disclosure. The embodiments described in the drawings and description are intended to be exemplary and not limiting. As used herein, the term 'exemplary' means 'serving as an example or illustration' and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Definitions

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

As used in the specification and claims, the singular form "a", "an", and "the" include both singular and plural references unless the context clearly dictates otherwise. For example, the term "an evoked potential" may include, and is contemplated to include, a plurality of evoked potentials. At times, the claims and disclosure may include terms such as "a plurality," "one or more," or "at least one;" however, the absence of such terms is not intended to mean, and should not be interpreted to mean, that a plurality is not conceived for a particular embodiment.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

System Overview

FIG. 1 depicts a block diagram of a system for stimulating a nerve and measuring the strength and fatigability of the muscles and neuromuscular junctions of patients receiving neuromuscular blockade agents in accordance with one embodiment of the present disclosure. In the depicted embodiment, the system 100, which may be coupled to a patient 101, includes, but is not limited to, one or more recording electrodes 102, one or more stimulating electrodes 103, a paralytic assessment device 104, and a display unit 106.

In some embodiments of the system 100, the stimulating electrodes 103 are configured for placement on or near the arms or legs of a patient 101 over peripheral nervous structures such as, for example, the ulnar nerves, median nerves, peroneal nerves, and/or posterior tibial nerves. In some embodiments, the stimulating electrodes 103 are intended for placement on a patient's skin on the wrists and ankles so that the electrodes are located over or near the ulnar nerves and posterior tibial nerves. Such a configuration allows for full patient monitoring of peripheral nerves (i.e., monitoring of nerves in all limbs). In other embodiments, the system 100 may be used for upper limb monitoring only; in such embodiments, the stimulating electrodes 103 may be intended for placement on the skin of a patient's wrists, for example, over or near the ulnar nerves only. The recording electrodes 102 of some embodiments are configured for placement over the wrists or ankles, or other location where muscular and neuromuscular junction response to the stimulation from the stimulating electrodes 103 can be measured.

In various embodiments, the paralytic assessment device 104 is electronically coupled to the recording electrodes 102 and stimulating electrodes 103 via a plurality of cables, or the electrodes may be wirelessly coupled thereto. The paralytic assessment device 104 of various embodiments forms part of, is coupled to, and/or includes a computing device, such as, for example, the computing device 200 described in further detail below with reference to FIG. 2. The paralytic assessment device 104 may include or be coupled to a pulse generator to provide stimulation via the stimulating electrodes 103. In various embodiments, the paralytic assessment device 104 is also electrically, electronically, and/or mechanically coupled to the display unit 160 via a link 150. In some embodiments, the link 150 is internal wiring or external cable. In some embodiments, the link 150 is a wireless communication link. For example, in some embodiments, the paralytic assessment device 104 is wirelessly coupled to the display unit 160 via Bluetooth® or other radiofrequency signal or via near field communications or a cellular signal.

The display unit 106 may display various information on a graphical user interface (GUI), such as, for example, but not limited to, biographical information of a patient, suggested locations of electrodes, stimulation parameters, areas being stimulated and recorded, baseline and current signal traces, historical trends in signals, relevant changes in signals, location of signal changes, quality of recorded signals, position of electrodes, alerts due to significant changes in signals, and proposed movements to mitigate detrimental signal changes. In addition, the display unit 106 may include an input user interface, which includes, for example, a touchscreen, buttons, and/or control inputs. According to some embodiments, the input user interface allows an operator to set up the initial monitoring layout and interact with the display unit 106 during monitoring to add additional information, view information in a different format, or respond to alerts. In some embodiments, the display unit 106 may allow override of a change in signal by an anesthesiologist or other medical personnel, etc., when a signal change is related to or attributable to a change in dose of anesthetic agent or some other event unrelated to positioning effect or neuromuscular blockade.

Various embodiments of the system 100 also include software that facilitates the automation of the system 100. Such software may be stored within memory and executed by a processor within the system 100. In various embodiments, the memory and processor are components of a computer, and in at least some such embodiments, the paralytic assessment device 104 forms part of, is coupled via a wired or wireless connection to, and/or includes said computer. Additionally, in some embodiments, the system 100 includes one or more user interfaces to receive inputs from a user and provide outputs to the user. Such user interfaces may form part of the computer or may be in electrical or wireless communication with the computer. The user interfaces of some embodiments further facilitate the automation of the system 100.

Figure 2:
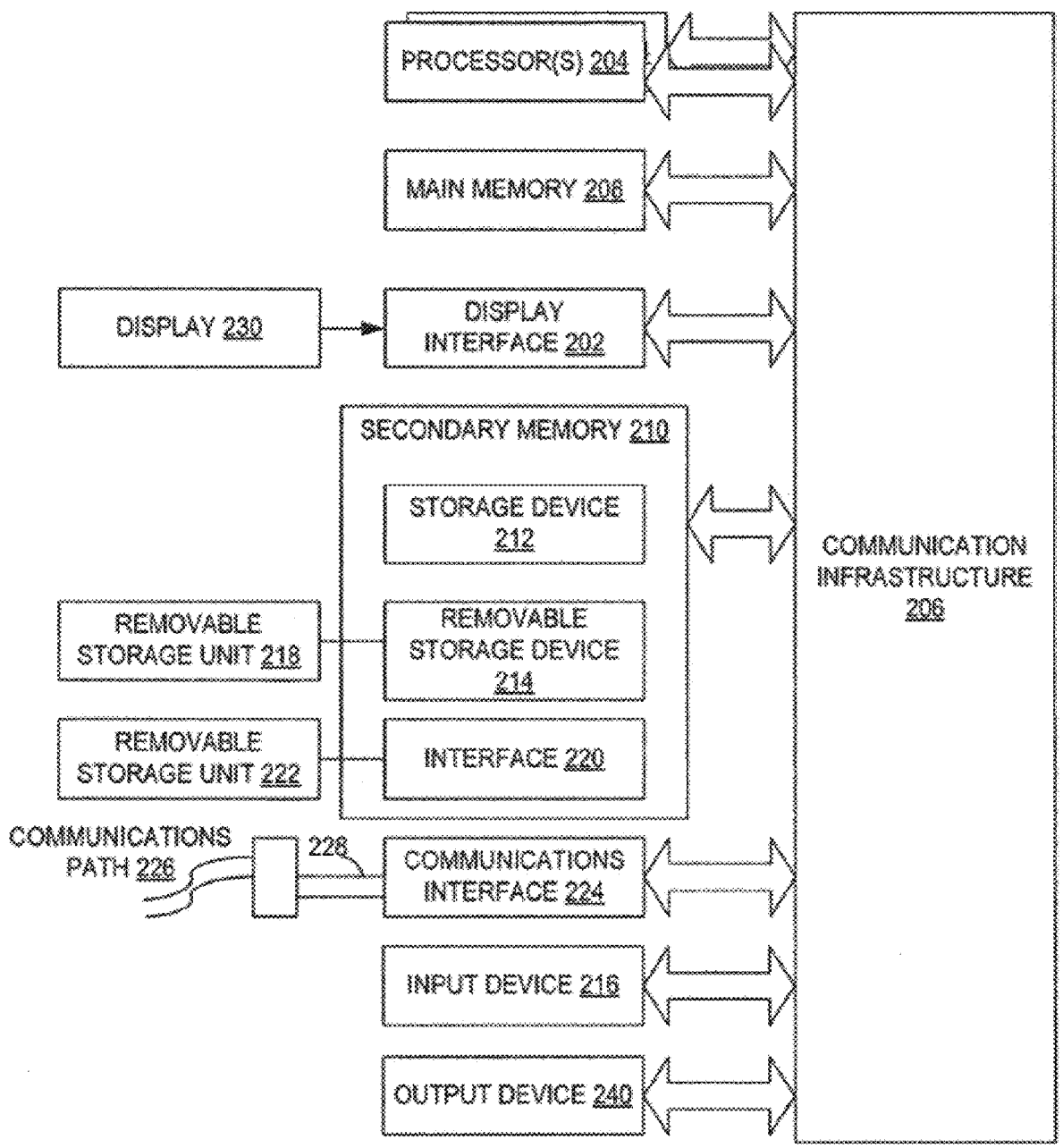
FIG. 2 depicts a functional block diagram of one embodiment of a computer system that may be used in association with, in connection with, and/or in place of any embodiment of the systems and components described herein.

The computing device 200 includes a processor and memory and stores programmed instructions. The instructions, when executed by the processor, cause the device to: (1) deliver stimulations (in the form of electric current or voltage) to the stimulating electrodes, and (2) record detected signals picked up at the recording electrodes. FIG. 2 depicts a block diagram of one example embodiment of a computer system that may form part of any of the systems described herein. Specifically, FIG. 2 illustrates an example computer 200, which may run an operating system such as, for example, MICROSOFT® WINDOWS® NT/98/2000/XP/CE/7/VISTA/RT/8, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., iOS or Mac/OS from APPLE® Corporation of Cupertino, Calif., U.S.A., or any of various versions of UNIX® (a trademark of the Open Group of San Francisco, Calif., USA) including, e.g., LINUX®, HPUX®, IBM AIX®, and SCO/UNIX®, or Android® from Google®, Inc. of Mountain View, Calif., U.S.A., etc. Such operating systems are provided for example only; the system embodiments described herein may be implemented on any appropriate computer system running any appropriate operating system.

Other potential components of the system 100, such as, for example, a computing device, a communications device, a personal computer (PC), a laptop computer, a tablet, a mobile device, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 2.

The computer system 200 may include one or more processors, such as processor(s) 204. The processor(s) 204 may be connected to a communication infrastructure 206 (for example, a communications bus, cross-over bar, or network, etc.). Various software embodiments may be described in terms of this example computer system. After reading this description, it will become apparent to a person skilled in the relevant art(s) how to implement the described methods using other computer systems and/or architectures.

Computer system 200 may include a display interface 202 to forward graphics, text, and other data, etc., from the communication infrastructure 206 for display on the display unit 230.

The computer system 200 may also include, e.g., but may not be limited to, a main memory 208, random access memory (RAM), and a secondary memory 210, etc. The secondary memory 210 may include, for example, (but may not be limited to) a hard disk drive 212 and/or a removable storage drive 214, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 214 may read from and/or write to a removable storage unit 218 in a well-known manner. Removable storage unit 218 may represent, for example, a floppy disk, a magnetic tape, an optical disk, a magneto-optical disk, a compact disk, a flash memory device, etc. which may be read from and written to by removable storage drive 214. As will be appreciated, the removable storage unit 218 may include a computer usable storage medium having stored therein computer software and/or data.

In alternative exemplary embodiments, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as, e.g., but not limited to, those found in some video game devices), a removable memory chip (such as, e.g., but not limited to, an erasable programmable read only memory (EPROM), or programmable read only memory (PROM) and associated socket, and other removable storage units 222 and interfaces 220, which may allow software and data to be transferred from the removable storage unit 222 to computer system 200.

Computer 200 may also include an input device 216 such as, for example, a mouse or other pointing device such as a digitizer, a touchscreen, a microphone, a keyboard, and/or other data entry device. Computer 200 may also include output devices 240, such as, for example, a display 230 and/or display interface 202. Computer 200 may include input/output (I/O) devices such as a communications interface 224, a cable 228, and/or a communications path 226, etc. These devices may include but are not limited to a network interface card and modems. The communications interface 224 may allow software and data to be transferred between the computer system 200 and external devices. Examples of a communications interface 224 include, for example, a modem, a network interface (such as, e.g., an Ethernet card), a communications port, a Personal Computer Memory Card International Association (PCMCIA) slot and card, etc. Software and data transferred via the communications interface 224 may be in the form of signals 228 which may be electronic, electromagnetic, optical, or other signals capable of being received by the communications interface 224. These signals 228 may be provided to the communications interface 224 via, for example, a communications path 226 such as a channel. This channel 226 may carry signals 228, for example propagated signals, and may be implemented using, for example, wire or cable, fiber optics, a telephone line, a cellular link, a radio frequency (RF) link and other communications channels, etc.

In various embodiments described herein, wired networks may include any of a wide variety of well-known means for coupling voice and data communications devices together. In various embodiments described herein, wireless network types may include, but are not limited to, for example, code division multiple access (CDMA), spread spectrum wireless, orthogonal frequency division multiplexing (OFDM), 1G, 2G, 3G, or 4G wireless, Bluetooth, Infrared Data Association (IrDA), shared wireless access protocol (SWAP), "wireless fidelity" (Wi-Fi), WIMAX, and other IEEE standard 802.11-compliant wireless local area network (LAN), 802.16-compliant wide area network (WAN), and ultra-wideband (UWB) networks, etc.

Some embodiments may include or otherwise make reference to WLANs. Examples of a WLAN may include a shared wireless access protocol (SWAP) developed by Home radio frequency (HomeRF), and wireless fidelity (Wi-Fi), a derivative of IEEE 802.11, advocated by the wireless Ethernet compatibility alliance (WECA). The IEEE 802.11 wireless LAN standard refers to various technologies that adhere to one or more of various wireless LAN standards. An IEEE 802.11 compliant wireless LAN may comply with any of one or more of the various IEEE 802.11 wireless LAN standards including, for example, wireless LANs compliant with IEEE std. 802.11a, b, d, g, or n, such as, e.g., but not limited to, IEEE std. 802.11 a, b, d, g, and n (including, e.g., but not limited to IEEE 802.11g-2003, etc.), etc.

Some embodiments described herein are directed to the apparatuses and/or devices for performing the operations described herein. Such an apparatus may be specially constructed for the desired purposes, or it may comprise a general purpose device selectively activated or reconfigured by a program stored in the device to perform the specialized purpose.

Other embodiments described herein are directed to instructions stored on a machine-readable medium, which may be read and executed by a computing platform to perform operations described herein. A machine-readable medium may include any mechanism for storing or transmitting information in a form readable by a machine (e.g., a computer). For example, an exemplary machine-readable storage medium may include: read only memory (ROM); random access memory (RAM); magnetic disk storage media; optical storage media; magneto-optical storage media; flash memory devices; other exemplary storage devices capable of storing electrical, optical, acoustical, or other form of propagated signals (e.g., carrier waves, infrared signals, digital signals, etc.) thereon, and others. Computer programs (also called computer control logic), may include object oriented computer programs, and may be stored in main memory 208 and/or the secondary memory 210 and/or removable storage units 214, also called computer program products. Such computer programs, when executed, may enable the computer system 200 to perform the features of the present invention as discussed herein. In particular, the computer programs, when executed, may enable the processor or processors 204 to provide a method to control and/or manage operation of an EPDD according to an exemplary embodiment. Accordingly, such computer programs may represent controllers of the computer system 200.

Another exemplary embodiment is directed to a computer program product comprising a computer readable medium having control logic (computer software) stored therein. The control logic, when executed by the processor 204, may cause the processor 204 to perform functions described herein. In other embodiments, various functions described herein may be implemented primarily in hardware using, for example, but not limited to, hardware components such as application specific integrated circuits (ASICs), or one or more state machines, etc. Implementation of the hardware state machine so as to perform the functions described herein will be apparent to persons skilled in the relevant art(s). In some embodiments, described functions may be implemented using one or a combination of any of hardware, firmware, and software, etc.

As used herein, the terms "computer program medium" and "computer readable medium" may generally refer to media such as, e.g., but not limited to removable storage drive 214, a hard disk installed in hard disk drive and/or other storage device 212, and signals 228, etc. These computer program products may provide software to computer system 200. An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it may be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device/hardware or portion of a device that processes electronic data from registers and/or memory to transform that electronic data into other electronic data that may be stored in registers and/or memory. A "computing platform" may comprise one or more processors.

According to an exemplary embodiment, exemplary methods set forth herein may be performed by an exemplary one or more computer processor(s) adapted to process program logic, which may be embodied on an exemplary computer accessible storage medium, which when such program logic is executed on the exemplary one or more processor(s) may perform such exemplary steps as set forth in the exemplary methods.

In some embodiments, the systems and methods for assessing neuromuscular blockade, paralysis, or neuromuscular junction status can be combined with the systems, devices and methods described in U.S. Pat. No. 8,731,654, entitled "SYSTEM, METHOD, APPARATUS, DEVICE AND COMPUTER PROGRAM PRODUCT FOR AUTOMATICALLY DETECTING POSITIONING EFFECT," which is incorporated herein by reference in its entirety. In some embodiments, the combination with the devices and methods of '654 patent can provide the benefit of a multi-functionality system. In some cases, the devices and methods of the '654 patent can be supplemented with the addition of one or more additional electrodes, for example a stimulating electrode on the wrist, arm or hand of the patient. The systems, methods and devices can be further modified according to the other embodiments described herein as desired.

Methods and Functions

Embodiments described herein generally relate to improved devices and methods for measuring the degree of neuromuscular blockade in patients, generally caused by administration of a neuromuscular blockade agent prior to or during surgery, particularly in the range of blockade that is borderline for safety. Various embodiments relate to devices, systems, and methods for obtaining and processing the recorded signals in such a manner that interference from electric surgical devices is reduced or eliminated while the target biosignal is maintained.

The system 100 of various embodiments may include one or more features intended to automate stimulation and improve reproducibility and fidelity of the measurement of neuromuscular blockade. Various exemplary features are described below.

According to an exemplary embodiment, the paralytic assessment device 104 continuously or intermittently, either as directed by a user or automatically by an automated system, monitors the level of neuromuscular blockade during or throughout the surgery and adjusts a stimulation protocol. The adjustment may include one or more of an adjustment of the stimulation frequencies, the number of stimuli delivered, or other adjustment of the applied stimulation. The stimulation protocol may be adjusted according to the degree of blockade present, to thereby improve reproducibility and fidelity of the measurement.

According to an exemplary embodiment, the paralytic assessment device applies electrical stimulation to peripheral nerves of a patient by sending electrical signals to the stimulating electrodes 103 located on some or all of a patient's limbs. The recording electrodes 102, including a sensor, sense the intrinsic electrical activity of the nerve and muscle induced by the electrical stimulations at the nerves. The measured amplitude, or various other characteristics of the electrical activity, directly corresponds to the strength of the muscle response, and can be used to indicate the amount of neuromuscular blockade. Accordingly, it is possible to determine the impact that the blockade agent has on the patient during the surgery. Changes in the electrical activity of the muscle can be correlated directly to changes caused by addition of the blockade agent or administration of a blockade reversal agent.

Figure 3:
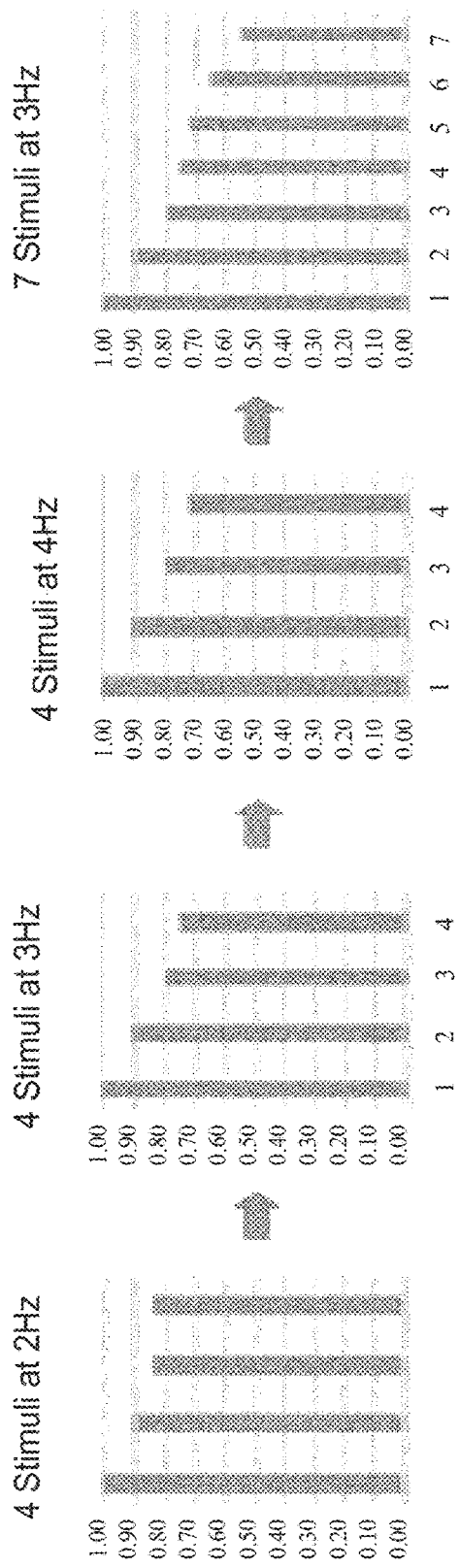
FIG. 3 is a series of graphs depicting the amplitude ratio between a first stimulus in a series to a last stimulus in a series at varying frequencies and quantities.
Figure 4:
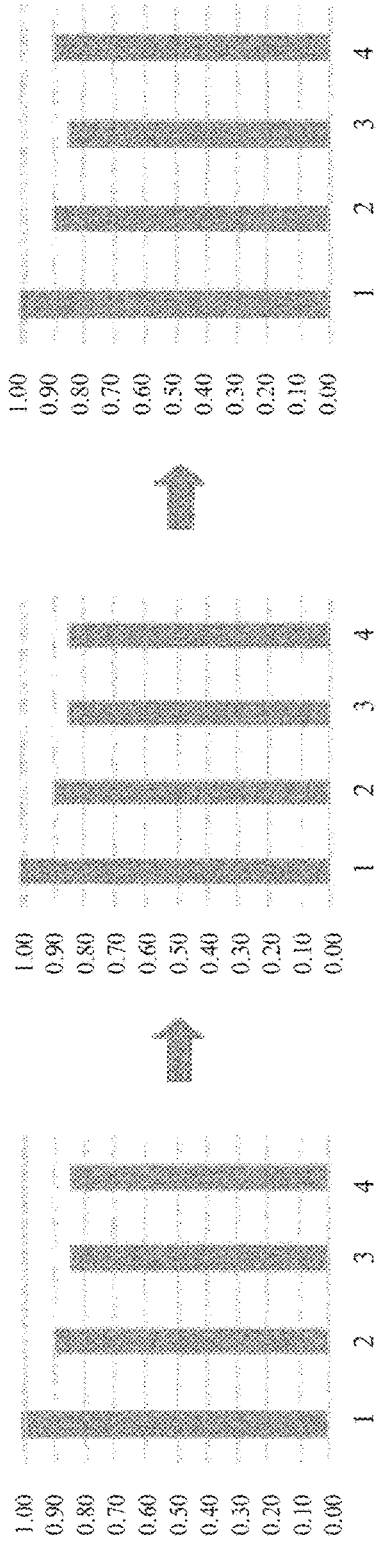
FIG. 4 is a series of graphs depicting the amplitude ratio between a first stimulus in a series to a last stimulus in a series at varying frequencies.

Neuromuscular blockade is generally measured utilizing one or more of a standardized set of stimuli applied at a specific frequency and for a specific period of time. Various embodiments of the device, however, instead can use stimulations applied in varying frequencies or length of trains to obtain a more apparent or better defined result. For instance, when train of four stimulation (TOF) is applied, the resulting ratio of the fourth muscle response to the first might fall in an unclear range, such as less than 1 but greater than 0.6. In various embodiments of the typical device this would trigger reapplication of the series of 4 stimulations at progressively higher frequencies such as 3 Hz, 4 Hz and so on in order to add additional stress to the neuromuscular junction and make its failure or integrity more apparent. As depicted in FIG. 3, the amplitude ratio of the first stimulus to the last stimulus was 0.85 for 4 stimuli at 2 Hz, which is within the margin of error to be considered a normal response to stimulation. However, by further stressing the neuromuscular junction with higher stimulation frequencies and a greater number of stimuli, the ratio of first to last stimulation decreased to a ratio of 0.55 which would clearly indicate that the junction is still not operating at a safe level of transmission. In another example, as depicted in FIG. 4 the amplitude ratio of the first stimulus to the last stimulus was 0.85 for 4 stimuli at 2 Hz which is within the margin of error to be considered a normal response to stimulation. By further stressing the neuromuscular junction with higher stimulation frequencies, the ratio of first to last stimulation increased to a ratio of 0.90 indicating that the junction is operating at a safe level of transmission and further testing is not required.

Some embodiments of the instant technology additionally, or alternatively, apply the stimuli in a longer train, for example, up to 8 stimuli or 12 stimuli and so on in order to add additional stress to the neuromuscular junction and to confirm accuracy of the result and make its failure or integrity more apparent.

Furthermore, in some embodiments the devices, systems and methods additionally, or alternatively, can apply the stimuli in progressively rapid fashion such that the interstimulus interval shrinks between successive stimuli as they are applied in order to add additional stress to the neuromuscular junction and make its failure or integrity more apparent Still further embodiments relate to applying repetitive stimulation at the same time that the stimulator is depolarizing the nerve to detect proximally recorded waveforms including somatosensory evoked potentials (SSEP) and updating the recording of neuromuscular blockade at the beginning of each SSEP average.

Other embodiments of the instant technology utilize amplifiers with one or more of CMRR of >96 dB, stimulation artifact filtering, and electro cautery detection, which can remove confounding factors from interpretation.

While most devices depend upon the user to initiate individual types of tests, various embodiments of the device, systems and methods disclosed herein use an automated algorithm for deciding when additional resolution of the degree of blockade is needed, and when or if additional stimuli at differing frequency or number of stimuli are needed. For example, the algorithm can be set for testing at predetermined intervals, upon readings below or above a desired threshold, in response to other physical parameters, in response to the stage or timing of a procedure, etc.

Some devices used to measure neuromuscular blockade depend upon direct wiring to the processing device. In some embodiments of the instant devices, systems and methods transmission may be via wireless signal.

Some devices also depend upon maximal single response from the muscle to measure neuromuscular blockade. In some embodiments disclosed herein, the devices, systems and methods use a graded progressive level of stimulations at a high rate of stimulation, for example, such as 20 Hz. In certain embodiments, the devices and methods deliver a minimal stimulation level, such as 10 mA, that will elicit responses from the first few motor units, to a maximal stimulation level, such as 40 mA, to elicit a maximal response from all motor units. Using a graded stimulation protocol such as this can more closely follow the physiological response that is natural for a person when contracting a muscle, and can provide greater fidelity of measurement of neuromuscular junction function.

Figure 5B:
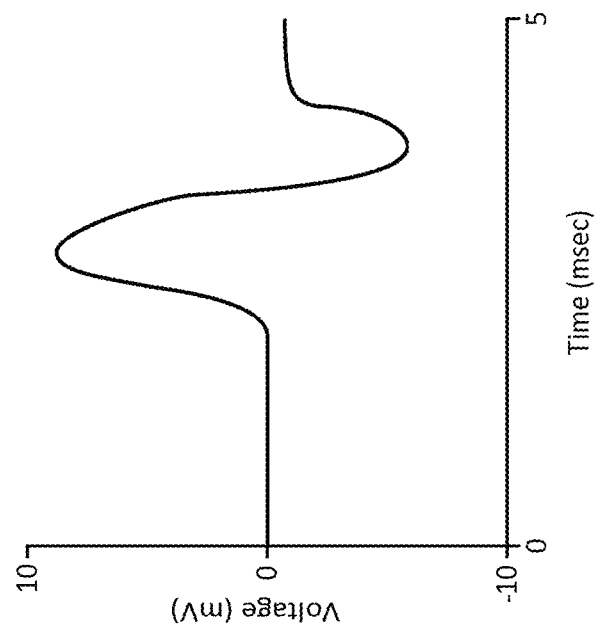
FIGS. 5A-5B provide a comparison for determining the onset of muscle response when the stimulus artifact has not been cleared (5A) and when a stimulus artifact has been removed by an adaptive filter (5B).
Figure 5A:
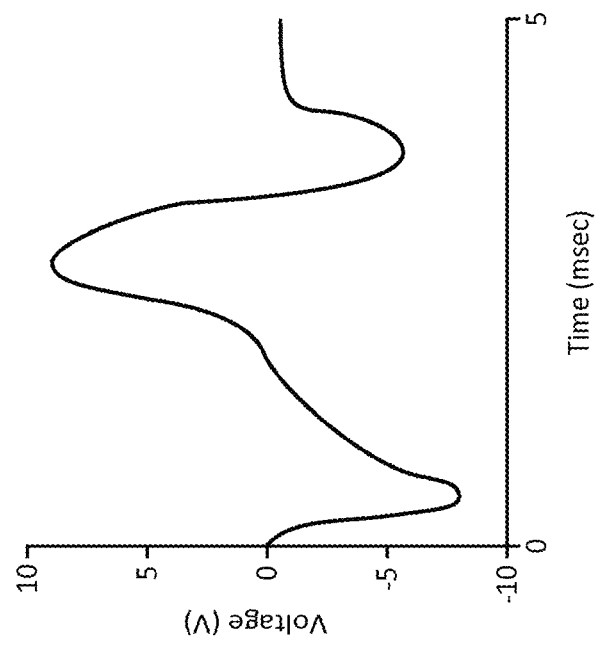

Some currently used devices can also have problems accurately measuring the onset of the evoked muscle response because the amplifiers have not recovered to baseline due to stimulus artifact contamination. In some embodiments, the instant devices, systems and methods can incorporate an adaptive filter algorithm that zeroes the baseline and to improve accuracy of the measurement of the muscle potentials. FIG. 5a displays stimulus artifact that has not recovered to baseline before the onset of the muscle response. This is improved in FIG. 5b which displays the use of an adaptive filter that removes the stimulus artifact, allowing for accurate measurement of the onset of the muscle response. It is important that the device be able to identify the onset of the potential in order to accurately quantify the muscle response.

Each of the following references is incorporated herein by reference in its entirety for all of the methods, devices, systems and components described therein, which can be incorporated with, substituted for, and/or combined with the systems, methods, devices and components described herein:

PCT/US2013/064518 Oct. 12, 2012 Apr. 17, 2014 Hampton et al. 'Neuromuscular monitoring display system'. This application describes a system for displaying a degree of neuromuscular block in a patient.

PCT/CA2004/002047 Nov. 26, 2003 Jun. 9, 2005 Bou-Phon Chang et. al. 'Monitoring of neuromuscular blockade using phonomyography'.

U.S. Pat. No. 4,291,705 Sep. 10, 1979 Sep. 29, 1981 A Severinghaus et. al. 'Neuromuscular Block Monitor'

U.S. Pat. No. 2,690,178 Nov. 13, 1950 Sep. 28, 1954 Research Corp 'Automatic apparatus for administering drugs'

U.S. Pat. No. 3,364,929 Dec. 21, 1964 Jan. 23, 1968 Burroughs Wellcome Co 'Method for administering muscle relaxant drug' U.S. Pat. No. 3,513,834 Nov. 21, 1967 May 26, 1970 Hitachi Ltd 'Anesthetic depth measuring system'

U.S. Pat. No. 3,565,080 Jul. 19, 1967 Feb. 23, 1971 Burroughs Wellcome Co 'Neuromuscular block monitoring apparatus'

U.S. Pat. No. 3,774,593 Dec. 27, 1971 Nov. 27, 1973 Shionogi & Co 'Method of and apparatus for sleep monitoring by brainwave, electromyographic and eye movement signals'

U.S. Pat. No. 3,898,983 Oct. 3, 1973 Aug. 12, 1975 James O Elam 'Device and method for detecting the degree of muscle relaxation of a medical patient'

U.S. Pat. No. 3,905,355 Dec. 6, 1973 Sep. 16, 1975 Joseph Brudny 'System for the measurement, display and instrumental conditioning of electromyographic signals'

U.S. Pat. No. 3,916,876 Jun. 13, 1974 Nov. 4, 1975 Fsw Associates 'Differential/ratiometric electromyographic bio-feedback monitor'

U.S. Pat. No. 4,148,303 Sep. 9, 1976 Apr. 10, 1979 Cohen Leonard 'A Method of assessing intentional muscular disability'

Kimura, J, Electrodiagnosis in Diseases of Nerve and Muscle Principles and Practice, 4th Ed., Oxford University Press, 2013 which describes Lien, C. A. & Kopman, A. F. (2014), 'Current recommendations for monitoring depth of neuromuscular blockade.', Curr Opin Anaesthesiol 27(6), 616-622

Ali, H. H. Monitoring of neuromuscular function. Seminars in Anaesthesia. 1984; 284-292.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

What is claimed is:

1. A system comprising:
    at least one stimulating electrode;
    at least one recording electrode; and
    a computing device comprising a processor having instructions stored thereon, wherein, when executed by the computing device, cause the computing device to:
        apply stimuli to a nerve of a patient through the stimulating electrode according to a stimulation protocol, wherein the stimulation protocol provides a plurality of stimulation sequences that vary in amplitude of the pulses in each stimulation sequence of the plurality of stimulation sequences, frequency of pulses in each stimulation sequence of the plurality of stimulation sequences, a frequency of each stimulation sequence of the plurality of stimulation sequences, a number of pulses in each stimulation sequence of the plurality of stimulation sequences, or all of the above;

measure, by the at least one recording electrode, electrical responses of a muscle;

estimate, by the computing device, a degree of neuromuscular blockade based on changes in the electrical responses of the muscle during a stimulation sequence of the plurality of stimulation sequences;

determine, by the computing device, if the stimulation protocol needs to be adjusted, wherein the computing device determines if the stimulation protocol needs to be adjusted at predetermined intervals, upon electrical response readings above or below a threshold value, in response to other physical parameters of the patient, and/or in concert with a timing procedure; and adjust, by the computing device based on the determination that the stimulation protocol needs to be adjusted, based on the estimated degree of neuromuscular blockade, and during the application of the stimuli according to the stimulation protocol, the stimulation protocol.

2. The system of claim 1, wherein estimating the degree of neuromuscular blockade comprises determining a ratio between the electrical response of the muscle from a first pulse in a stimulation sequence and the electrical response of the muscle from a last pulse in the stimulation sequence.

3. The system of claim 1, wherein when the stimulation protocol provides a plurality of stimulation sequences that vary in the number of pulses, the number of pulses is between four and twenty pulses.

4. The system of claim 3, wherein the number of pulses increases with each subsequent stimulation sequence in the stimulation protocol.

5. The system of claim 1, wherein when the stimulation protocol provides a plurality of stimulation sequences that vary in the frequency of pulses, the frequency of pulses is between 2 Hz and 10 Hz.

6. The system of claim 5, wherein the frequency of pulses increases with each subsequent stimulation sequence in the stimulation protocol.

7. The system of claim 1, wherein the stimulation protocol comprises a first stimulation sequence of four pulses at a first frequency, a second stimulation sequence of four pulses at a second frequency higher than the first frequency, a third stimulation sequence of four pulses at a third frequency higher than the second frequency.

8. The system of claim 7, wherein the stimulation protocol further comprises a fourth stimulation sequence of more than four pulses.

9. The system of claim 1, wherein the processor further comprises instructions that when executed by the computing device, cause the computing device to function automatically, without user input.

10. The system of claim 9, wherein the computing device automatically determines if the stimulation protocol needs to be adjusted and adjusts the stimulation protocol.

11. The system of claim 1, wherein the nerve is a peripheral nerve.

12. The system of claim 11, wherein the peripheral nerve is at least one of the nerves in a group comprising: an ulnar nerve, a median nerve, a peroneal nerve, and a posterior tibial nerve.

13. The system of claim 1, wherein the stimulating electrode is configured to be positioned on a wrist or an ankle of a patient.

14. The system of claim 1, further comprising a display unit for displaying information about a patient.

15. The system of claim 14, wherein the information is information related to the degree of neuromuscular blockade.

16. A computerized method for estimating the degree of neuromuscular blockade, comprising:

applying stimuli to a nerve through a stimulating electrode according to a stimulation protocol, wherein the stimulation protocol provides a plurality of stimulation sequences comprising a plurality of pulses that vary in amplitude of pulses in each stimulation sequence of the plurality of stimulation sequences, frequency of pulses in each stimulation sequence of the plurality of stimulation sequences, frequency of each stimulation sequence of the plurality of stimulation sequences, number of pulses in each stimulation sequence of the plurality of stimulation sequences, or all of the above;

measuring, by a recording electrode, electrical responses of a muscle;

estimating, by a computing device coupled to the stimulating electrode and the recording electrode, a degree of neuromuscular blockade based on changes in the electrical responses of the muscle during a stimulation sequence of the plurality of stimulation sequences;

determining, by the computing device, if the stimulation protocol needs to be adjusted, based on the estimation of the degree of neuromuscular blockade; and adjusting, by the computing device based on the determination that the stimulation protocol needs to be adjusted, based on the estimated degree of neuromuscular blockade, and during the application of the stimuli according to the stimulation protocol, the stimulation protocol.

17. The method of claim 16, wherein estimating the degree of neuromuscular blockade comprises determining a ratio between the electrical response of the muscle from a first pulse in a stimulation sequence and the electrical response of the muscle from a last pulse in the stimulation sequence.

18. The method of claim 16, wherein the nerve is a peripheral nerve.

19. The method of claim 18, wherein the peripheral nerve is at least one of the nerves in a group comprising: an ulnar nerve, a median nerve, a peroneal nerve, and a posterior tibial nerve.

20. The method of claim 16, wherein the stimulating electrode is positioned on a wrist or an ankle of a patient.

21. The method of claim 16, wherein the stimulation protocol comprises a first stimulation sequence of four pulses at a first frequency, a second stimulation sequence of four pulses at a second frequency higher than the first frequency, a third stimulation sequence of four pulses at a third frequency higher than the second frequency.

22. The method of claim 21, wherein the stimulation protocol further comprises a fourth stimulation sequence of more than four pulses.

23. The method of claim 16, wherein information related to the degree of neuromuscular blockade is displayed on a display unit.

24. The method of claim 16, wherein the computing device determines if the stimulation protocol needs to be adjusted at predetermined intervals, upon electrical response readings above or below a threshold value, in response to other physical parameters of the patient, and/or in concert with a timing of a procedure.

25. A system for estimating the degree of neuromuscular blockade, the system comprising a computing device comprising a processor having instructions stored thereon, wherein, when executed by the computing device, cause the computing device to provide a first set of electrical stimuli to a nerve according to a stimulation protocol; measure muscle responses to the stimuli; estimate, based on the measured muscle responses, the degree of neuromuscular blockade; determine, based on the estimation, if the stimulation protocol needs to be adjusted; and automatically adjust the stimuli by varying at least one of the amplitude, frequency, or number of pulses in a second set of stimuli.

26. A computerized method for estimating the degree of neuromuscular blockade comprising providing a first set of electrical stimuli to a nerve according to a stimulation protocol; measuring muscle responses to the stimuli; estimating, based on the measured muscle responses, the degree of neuromuscular blockade; determining, based on the estimation, if the stimulation protocol needs to be adjusted; and automatically adjusting the stimuli by varying at least one of the amplitude, frequency, or number of pulses in a second set of stimuli.

* * * * *